United States Patent [19]

Brandes et al.

[11] Patent Number: 4,623,653

[45] Date of Patent: Nov. 18, 1986

[54] FUNGICIDAL COMPOSITIONS EMPLOYING SYNERGISTIC MIXTURES OF A SUBSTITUTED 1-HYDROXYETHYL-TRIAZOLE AND TRIADIMEFON

[75] Inventors: Wilhelm Brandes, Leichlingen; Gerd Hänssler, Leverkusen; Paul Reinecke, Leverkusen; Hans Scheinpflug, Leverkusen; Graham Holmwood, Wuppertal, all of Fed. Rep. of Germany

[73] Assignee: Bayer Aktiengesellschaft, Leverkusen, Fed. Rep. of Germany

[21] Appl. No.: 644,749

[22] Filed: Aug. 27, 1984

[30] Foreign Application Priority Data

Sep. 16, 1983 [DE] Fed. Rep. of Germany ....... 3333412

[51] Int. Cl.[4] ........................................ A01N 43/64

[52] U.S. Cl. ................................................ 514/383

[58] Field of Search ....................... 424/269; 514/383

[56] References Cited

U.S. PATENT DOCUMENTS 4,251,512 2/1981 Brandes et al. .................... 424/162

FOREIGN PATENT DOCUMENTS 0040345 11/1981 European Pat. Off. .

0061835 10/1982 European Pat. Off. .

*Primary Examiner*—Allen J. Robinson

*Attorney, Agent, or Firm*—Sprung Horn Kramer & Woods

[57] ABSTRACT

Synergistic fungicidal compositions comprising (i) a substituted 1-hydroxyethyl-triazole of the formula

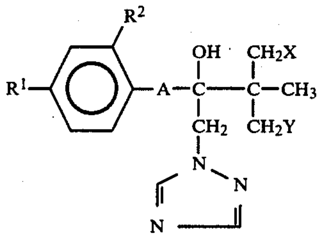

in which $R^1$, $R^2$, X, Y and A have various meanings, or addition products thereof with acids or metal salts, and (ii) at least one of (A) wettable sulphur,
(B) a polyhalogenoalkylthio derivative,
(C) a quanidine derivative,
(D) an aromatic acid lactone,
(E) a dithiocarbamate,
(F) a benzimidazole derivative,
(G) an imidazole or triazole derivative,
(H) a phosphoric acid ester,
(I) a tetrahydroquinoline derivative,
(J) an S, N-heterocyclic compound,
(K) a urea derivative,
(L) a sulphonamide derivative,
(M) a polyhydroxyether derivative,
(N) a triazine derivative,
(O) a copper-hydroxy quinoline complex,
(P) an N-formul derivative,
(Q) a morpholine derivative,
(R) a quinoxaline derivative, and
(S) a dicarboxamide derivative.

1 Claim, No Drawings

FUNGICIDAL COMPOSITIONS EMPLOYING SYNERGISTIC MIXTURES OF A SUBSTITUTED 1-HYDROXYETHYL-TRIAZOLE AND TRIADIMEFON

The present invention relates to new fungicidal active compound combinations of special known substituted 1-hydroxyethyl-triazolyl derivatives and other known fungicidal active compounds.

It is generally known that mixtures containing 1,2,4-triazole derivatives, such as, for example, 1-(4-chlorophenoxy)-3,3-dimethyl-1-(1,2,4-triazol-1-yl)-2-butanone, in combination with other known fungicides have a substantially greater action than the individual components. See U.S. Pat. No. 31,693. However, the activity of the active compound mixtures is not completely satisfactory in all fields of use.

It has been found that new active compound combinations of special substituted 1-hydroxyethyl-triazolyl derivatives of the formula (I)

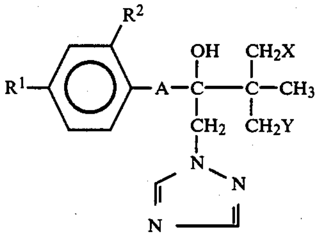

in which $R^1$ represents chlorine, phenyl, methoximinomethyl or 1-methoximinoethyl, $R^2$ represents hydrogen, methyl or chlorine, X and Y are identical or different and represent hydrogen, fluorine or chlorine and A represents the grouping $-OCH_2-$, and also represents the grouping $-CH_2CH_2-$ when X and/or Y represent fluorine or chlorine, and their acid addition salts and metal salt complexes and (A) wettable sulphur and/or (B) polyhalogenoalkylthio derivatives of the formulae

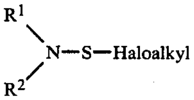

(IIa)

$R^1 = (CH_3)_2N-SO_2-$, $R^2 =$ 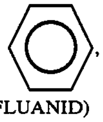, Haloalkyl $= -CCl_2F$ (DICHLOFLUANID)

(IIb)

$R^1$ and $R^2 =$ 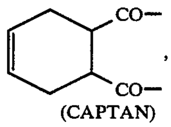, Haloalkyl $= CCl_3$ (CAPTAN)

-continued (IIc)

$R^1$ and $R^2 =$ 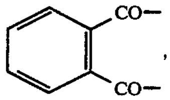, Haloalkyl $= -CCl_3$ (FOLPET)

(IId)

$R^1$ and $R^2 =$ 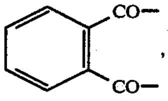, Haloalkyl $= -CCl_2-CHCl_2$ (CAPTAFOL)

and/or (C) a guanidine derivative of the formula (III)

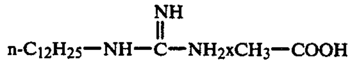

(DODINE)

and/or (D) an aromatic carboxylic acid derivative of the formula (IV)

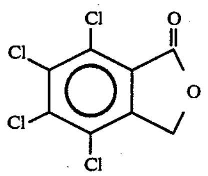

(TETRACHLOROPHTHALIDE)

and/or (E) dithiocarbamates of the formulae

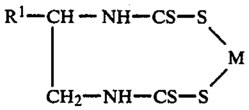

$R^1 = H, M = Zn$ (Va)
(ZINEB)

$R^1 = H, M = Mn$ (Vb)
(MANEB)

mixture of (Va) and (Vb) (Vc)
(MANCOZEB)

$R^1 = CH_3, M = Zn$ (Vd)
(PROPINEB)

and/or (F) benzimidazole derivatives of the formulae (VIa)

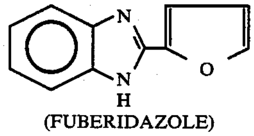

(FUBERIDAZOLE)

(VIb)

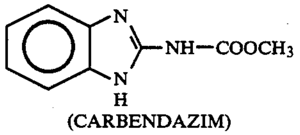

(CARBENDAZIM)

and/or (G) derivatives of imidazoles and triazoles of the formulae

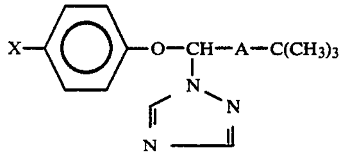

X = Cl, A = CO (VIIa)
(TRIADIMEFON)

X = Cl, A = CH(OH) (VIIb)
(TRIADIMENOL)

(VIIc)

X = , A = CH(OH)

(BITERTANOL)

(VIId)

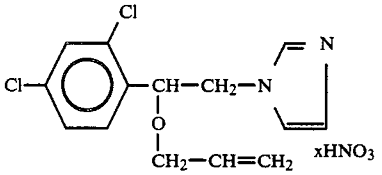

(FUNGAFLOR)

(VIIe)

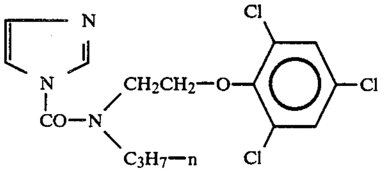

(PROCHLORAZ)

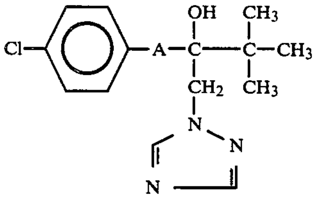

A = —$CH_2CH_2$— (VIIf)

A = —CH=CH— (VIIg)

and/or (H) a phosphoric acid ester of the formula (VIII)

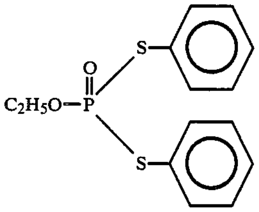

(EDIFENPHOS)

and/or (I) a tetrahydroquinoline derivative of the formulae

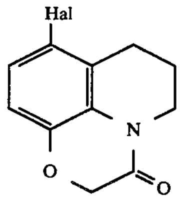

Hal = Br (IXa)

Hal = Cl (IXb)

(IXc)

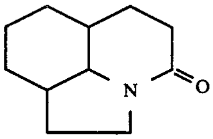

(LILOLIDONE)

and/or (J) S,N-heterocyclic compounds of the formulae (Xa)

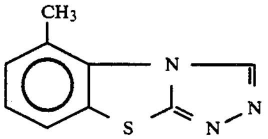

(TRICYCLAZOLE)

(Xb)

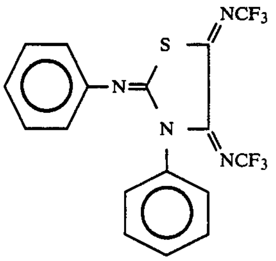

(FLUBENZIMINE)

and/or (K) a urea derivative of the formula (XI)

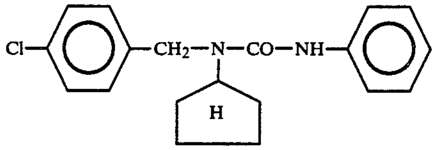

(PENCYCURON)

and/or (L) a sulphonamide derivative of the formula (XII)

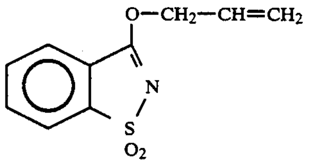

(PROBENAZOLE)

and/or (M) a polyhydroxyether derivative of the formula

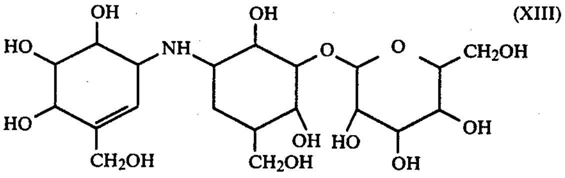

(XIII)

(VALIDAMYCIN)

and/or (N) a triazine derivative of the formula

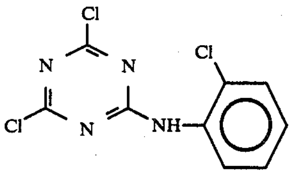

(XIV)

(ANILAZINE)

and/or (O) a copper complex salt of the formula

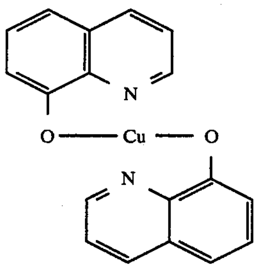

(XV)

(COPPER OXINATE)

and/or (P) an N-formyl derivative of the formula

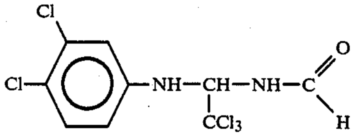

(XVI)

(CHLORANIFORMETHAN)

and/or (Q) morpholine derivatives of the formulae

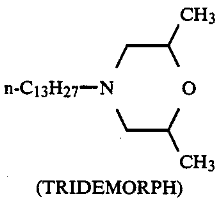

(XVIIa)

(TRIDEMORPH)

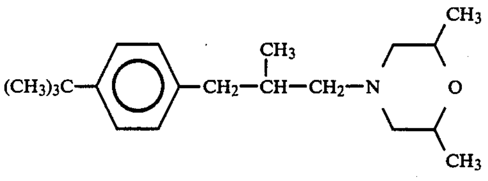

(XVIIb)

-continued (FENPROPEMORPH)

and/or (R) a quinoxaline derivative of the formula

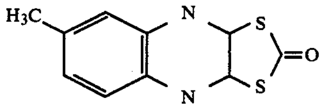

(XVIII)

(CHINOMETHIONAT)

and/or (S) a dicarboximide derivative of the formulae

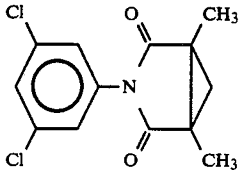

(XIXa)

(PROCYMIDONE)

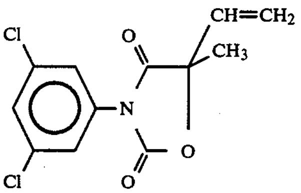

(XIXb)

(VINCHLOZOLIN)

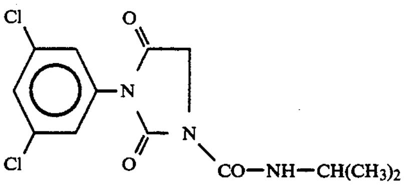

(XIXc)

(IPRODIONE)

have a particularly high fungicidal activity.

Surprisingly, the fungicidal action of the active compound combinations according to the invention is substantially higher than the action of the individual components and, where relevant, than the sum of the individual components (synergistic effect). The discovery of these combinations of special compounds of the formula (I) and the active compounds of the abovementioned groups (A), (B), (C), (D), (E), (F), (G), (H), (I), (J), (K), (L), (M), (N), (O), (P), (Q), (R) and (S) thus represents a valuable enrichment of the art.

Formula (I) above gives an unambiguous definition of the substituted 1-hydroxyethyl-triazolyl derivatives specially to be used for the combination according to the invention; this formula preferably embraces the following compounds:

(Ia) $R^1$=Cl, $R^2$=H, X=F, Y=H, A=$-CH_2CH_2-$ (Ib) $R^1$=$CH_3ON$=CH—, $R^2$=H, X=H, Y=H, A=$-OCH_2-$ (Ic)

$R^1$ = 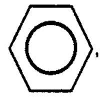, $R^2$=H, X=H, Y=H, A=$-OCH_2-$ (Id) $R^1$=Cl, $R^2$=$CH_3$, X=H, Y=H, A=$-OCH_2-$ (Ie) $R^1$=Cl, $R^2$=$CH_3$, X=F, Y=H, A=$-OCH_2-$ (If) $R^1$=Cl, $R^2$=Cl, X=F, Y=H, A=$-OCH_2-$ (Ig) $R^1$=Cl, $R^2$=H, X=F, Y=F, A=$-CH_2CH_2-$ (Ih) $R^1$=$CH_3ON{=}C(CH_3)-$, $R^2$=H, X=H, A=$-OCH_2-$ The stated compounds of the formula (I) have been described; see U.S. Ser. No. 260,479 filed May 4, 1981, now abandoned, Ser. Nos. 458,086 filed Jan. 14, 1983, now abandoned, and 534,233 filed Sept. 21, 1983, now pending.

The compounds which are to be used as components for the mixture and which belong to the abovementioned groups (A), (B), (C), (D), (E), (F), (G), (H), (I), (J), (K), (L), (M), (N), (O), (P), (Q), (R) and (S) have been described in the literature; in this context, see the following references:

(A): R. Wegler, 'Chemie der Pflanzenschutz- und Schädlingsbekämpfungsmittel' (Chemistry of Plant Protection Agents and Pest-Combating Agents), Volume 2, page 51, Springer Verlag Berlin Heidelberg/New York, 1970;

(B): R. Wegler, loc. cit., pages 95, 108, 109 and 110;

(C): R. Wegler, loc. cit., page 70;

(D): K. H. Büchel, 'Pflanzenschutz und Schädlingsbekämpfung' (Plant Protection and Pest-Combating', page 146, Georg Thieme Verlag, Stuttgart, 1977;

(E): R. Wegler, loc. cit., pages 65 and 66;

(F): DE-AS (German Published Specification) No. 1,209,799, DE-OS (German Published Specification) No. 1,932,297, U.S. Pat. No. 3,010,968;

(G): DE-AS (German Published Specification) No. 2,201,063, DE-AS (German Published Specification) No. 2,324,010, DE-OS (German Published Specification) No. 2,063,857, DE-AS (German Published Specification) No. 2,429,523, DE-OS (German Published Specification) No. 3,018,866;

(H): R. Wegler, loc. cit., page 132;

(I): German Patent Application P No. 32 34 529 of 17.9.1982 [LeA 21 962], U.S. Pat. No. 3,917,838;

(J): DE-OS (German Published Specification) No. 2,250,077, DE-OS (German Published Specification) No. 2,062,348;

(K): DE-OS (German Published Specification) No. 2,732,257;

(L): K. H. Büchel, loc. cit., page 142;

(M): Chem. Commun. 1972, No. 12, pages 747-748;

(N): R. Wegler, loc. cit., page 120;

(O): R. Wegler, loc. cit., page 112;

(P): R. Wegler, loc. cit., page 97

(Q): K. H. Büchel; loc. cit., page 149; DE-OS (German Published Specification) No. 2,656,747;

(R): R. Wegler, loc. cit., page 128 and (S): K. H. Büchel, loc. cit., page 148.

Preferred active compound combinations are those comprising the substituted 1-hydroxyethyl-triazolyl derivatives of the formula (Ia), (Ib), (Ic), (Id), (Ie), (If), (Ig) or (Ih) and an active compound of the formulae (IIa), (IIb), (IIc) or (IId); and/or an active compound of the formula (III); and/or an active compound of the formula (IV); and/or an active compound of the formulae (Va), (Vb), (Vc) or (Vd); and/or an active compound of the formulae (VIIe); and/or an active compound of the formula (VIII); and/or an active compound of the formula (IXa); and/or an active compound of the formula (Xa); and/or an active compound of the formula (XI); and/or an active compound of the formula (XII); and/or an active compound of the formula (XIII).

An active compound combination consisting of the 2,2-bisfluoromethyl-5-cyclohexyl-4-(1,2,4-triazol-1-yl)-3-pentanols of the formula (I) and the active compounds from the groups (A) and/or (B) and/or (C) and/or (D) and or (E) and/or (F) and/or (G) and/or (H) and/or (I) and/or (J) and/or (K) and/or (L) and/or (M) and/or (N) and/or (O) and/or (P) and/or (Q) and/or (R) and/or (S) can also contain further active compounds (for example as a third component).

The weight ratios of the active compound groups in the active compound combinations can vary within relatively wide ranges. In general, 0.01 to 500 parts by weight of active compound from the active compound classes (A) to (S), preferably 0.02 to 200 parts by weight of the latter, particularly preferably 0.1 to 50 parts by weight, are employed per part by weight of the compound of the formula (I).

The active compound combinations according to the invention exhibit a powerful microbicidal action and can be employed in practice for combating undesired microorganisms; they are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Dueteromycetes.

The good toleration, by plants, of the active compound combinations, at the concentrations required for combating plant diseases, permits treatment of aboveground parts of plants, of vegetative propagation stock and seeds, and of the soil.

The active compound combinations according to the invention have a very broad spectrum of action and can be used against parasitic fungi which infect aboveground parts of plants or attack the plants through the soil, as well as against seed-borne pathogens. Such active compound combinations are of particular practical importance as seed dressings against phytopathogenic fungi which are borne with the seed or occur in the soil and infect the crop plants from there. The diseases involved are seedling diseases, root rots and stalk, stem, leaf, bloom, fruit and seed diseases, which are caused, in particular, by Tilletia, Urocystis, Ustilago, Septoria, Typhula, Rhynchosporium, Helminthosporium and Fusarium species. As a result of the systemic action of one of the components of the mixture, the plants are also often protected, for a relatively long time after dressing, from pathogens which can attack various parts of the shoot, for example powdery mildew fungi and rust fungi. In addition, the active compound combinations can also be employed as soil-treatment agents against phytopathogenic fungi, and are effective against root rots and Tracheomycoses which are caused by, for example, pathogens of the genera pythium, Verticillium, Phialophora, Rhizoctonia, Fusarium and Thielaviopsis.

However, when applied to the above-ground parts of plants, the active compound combinations according to the invention also exhibit an excellent action against pathogens on various crop plants, such as powdery mildew fungi (Erysiphe, Uncinula, Sphaerotheca and Podosphaera species and *Leveillula taurica*), rust fungi, Venturia species, Cercospora species, Alternaria species, Botrytis species, Phytophthora species, Peronospora species, Fusarium species, Pyrenophora species, Cochliobolus species, Septoria species, *Pseudocercosporella herpotrichoides, Pyricularia oryzae* and *Pellicularia sasakii.*

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The following use examples serve as illustrations.

EXAMPLE A

Pyricularia test (rice)/protective

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried, the plants are inoculated with an aqueous spore suspension of *Pyricularia oryzae.* The plants are then placed in a greenhouse at 100% relative atmospheric humidity and 25° C.

Evaluation of the disease infestation is carried out 4 days after the inoculation.

In order to demonstrate a synergistic effect between the active compounds used in these tests, the results were evaluated by the method described by R. S. Colby (Calculating Synergistic and Antagonistic Responses of Herbicide Combinations: Weeds 15, 20–22, 1967). The expected infestation, in %, of the untreated control (E) was calculated in accordance with the equation $E=[(x \cdot y)/100]$ In this equation, X and Y denote the disease infestation—expressed as a % of the untreated control—which is permitted by the two preparations when applied separately. A synergistic effect is present when the fungicidal action of the active compound combinations is greater than that of the individual active compounds applied. In this case, the infestation actually observed must be less than the value for the expected infestation (E), calculated from the formula given above.

TABLE A

Pyricularia test (rice) / protective

| Active compound | Active compound concentration in % | Disease infestation as a % of the untreated control |
|---|---|---|
| (Ia) (known) | 0.0025 | 20 |
| | 0.001 | 50 |
| (Ib) (known) | 0.0025 | 50 |
| | 0.001 | 70 |
| (IV) (known) | 0.001 | 70 |
| (TETRACHLORO-PHTHALIDE) | 0.0005 | 90 |
| (XII) (known) | 0.001 | 50 |
| (PROBENAZOLE) | 0.0005 | 70 |
| (VIIe) (known) | 0.001 | 70 |
| (PROCHLORAZ) | 0.0005 | 70 |
| (IXa) (known) | 0.001 | 50 |
| | 0.0005 | 90 |

| Active compound | Active compound concentration in % | Observed infestation after application of the mixture as a % of the untreated control | Expected infestation of (E) after application of the mixture as a % of the untreated control |
|---|---|---|---|
| Mixture of (Ia) and (XII) (mixing ratio 5:1) | 0.0025 + 0.0005 | 10 | 14 |
| Mixture of (Ia) and (XII) (mixing ratio 1:1) | 0.001 + 0.001 | 10 | 25 |
| Mixture of (Ia) and (XII) (mixing ratio 2:1) | 0.001 + 0.0005 | 15 | 35 |
| Mixture of (Ia) and (IXa) (mixing ratio 1:1) | 0.001 + 0.001 | 20 | 25 |
| Mixture of (Ia) and (IXa) (mixing ratio 2:1) | 0.001 + 0.0005 | 40 | 45 |
| Mixture of (Ib) and (IV) (mixing ratio 2.5:1) | 0.0025 + 0.001 | 20 | 35 |
| Mixture of (Ib) and (VIIe) (mixing ratio 1:1) | 0.001 + 0.001 | 30 | 49 |
| Mixture of (Ib) and (VIIe) (mixing ratio 2:1) | 0.001 + 0.0005 | 30 | 49 |

EXAMPLE B

Pellicularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In order to demonstrate a synergistic effect between the active compounds used in these tests, the results were evaluated by the method described by R. S. Colby (Calculating Synergistic and Antagonistic Responses of Herbicide Combinations: Weeds 15, 20–22, 1967). The expected infestation, in %, of the untreated control (E) was calculated in accordance with the equation $E=[(X \cdot Y)/100]$ In this equation, X and Y denote the disease infestation—expressed as a % of the untreated control—which is permitted by the two preparations when applied separately. A synergistic effect is present when the fungicidal action of the active compound combination is greater than that of the individual active compounds applied. In this case, the infestation actually observed must be less than the value for the expected infestation (E), calculated from the formula given above.

TABLE B

Pellicularia test (rice) / protective

| Active compound | Active compound concentration in % | Disease infestation as a % of the untreated control |
|---|---|---|
| (Ia) (known) | 0.0025 | 20 |
| | 0.001 | 30 |
| | 0.0005 | 100 |
| (Ib) (known) | 0.0025 | 50 |
| (XI) (known) (PENCYCURON) | 0.0001 | 70 |
| (XIII) (known) | 0.001 | 30 |
| (VALIDAMYCIN) | 0.0005 | 70 |

| Active compound | Active compound concentration in % | Observed infestation after application of the mixture as a % of the untreated control | Expected infestation after application of the mixture as a % of the untreated control |
|---|---|---|---|
| Mixture of (Ia) and (XI) (mixing ratio 25:1) | 0.0025 + 0.0001 | 10 | 14 |
| Mixture of (Ia) and (XI) (mixing ratio 10:1) | 0.001 + 0.0001 | 10 | 21 |
| Mixture of (Ia) and (XI) (mixing ratio 5:1) | 0.0005 + 0.0001 | 40 | 70 |
| Mixture of (Ia) and (XIII) (mixing ratio 5:1) | 0.0025 + 0.0005 | 10 | 14 |
| Mixture of (Ia) and (XIII) (mixing ratio 2:1) | 0.001 + 0.0005 | 10 | 21 |
| Mixture of (Ib) and (XIII) (mixing ratio 2.5:1) | 0.0025 + 0.001 | 10 | 15 |
| Mixture of (Ib) and (XIII) (mixing ratio 5:1) | 0.0025 + 0.0005 | 10 | 35 |

EXAMPLE C

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea.*

The plants are then placed in a greenhouse at 23° to 24° C. and at a relative atmospheric humidity of about 75%.

Evaluation is carried out 10 days after the inoculation.

TABLE C

| Sphaerotheca test (cucumber) / protective | | |
|---|---|---|
| Active compound | Infestation in % in the case of an active compound concentration of | |
| Wettable sulphur (known) | 0.0025 | 60 |
| (VIIa) (known) (TRIADIMEFON) | 0.000025 | 67 |
| (Ic) (known) | 0.00005 | 75 |
| | 0.000025 | 87 |
| (Ia) (known) | 0.00005 | 63 |
| | 0.000025 | 57 |
| Mixture of (Ic) and wettable sulphur (mixing ratio 1:50) | 0.00005 0.0025 | 18 |
| Mixture of (Ia) and wettable sulphur (mixing ratio 1:50) | 0.00005 + 0.0025 | 16 |
| Mixture of (Ic) and (VIIa) (mixing ratio 1:1) | 0.000025 + 0.000025 | 45 |
| Mixture of (Ia) and (VIIa) (mixing ratio 1:1) | 0.000025 + 0.000025 | 30 |

EXAMPLE D

Erysiphe test (barley)/protective

Solvent: 100 parts by weight of dimethylformamide

Emulsifier: 0.25 parts by weight of alkylaryl polyglycol ether

To produce a suitable preparation of active compound 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In order to demonstrate a synergistic effect between the active compounds used in these tests, the results were evaluated by the method described by R. S. Colby (Calculating Synergistic and Antagonistic Responses of Herbicide Combinations: Weeds 15, 20-22, 1967). The expected infestation, in %, of the untreated control was calculated in accordance with the equation $$E=[(X \cdot Y)/100]$$

In this equation, X and Y denote the disease infestation—expressed as a % of the untreated control—which is permitted by the two preparations when applied separately. A synergistic effect is present when the fungicidal action of the active compound combination is greater than that of the individual active compounds applied. In this case, the infestation actually observed must be less than the value for the expected infestation (E), calculated from the formula given above.

TABLE D

| Erysiphe test (barley) / protective | | | |
|---|---|---|---|
| Active compound | Active Compound concentration in the spray liquor in % by weight | Disease infestation as a % of the untreated control | |
| (Ib) (known) | 0.00025 | 100 | |
| (Vd) (known) (PROPINEB) | 0.025 | 51.9 | |
| | | Observed infestation after application of the mixture as a % of the untreated control | Expected infestation (E) after application of the mixture as a % of the untreated control |
| Mixture of (Ib) and (Vd) (mixing ratio 1:100) | 0.00025 0.025 | 16.2 | 51.9 |

EXAMPLE E

Leptosphaeria nodorum test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In order to demonstrate a synergistic effect between the active compounds used in these tests, the results were evaluated by the method described by R. S. Colby (Calculating Synergistic and Antagonistic Responses of Herbicide Combinations: Weeds 15, 20-22, 1967). The expected infestation, in %, of the untreated control was calculated in accordance with the equation $$E=(X \cdot Y)/100$$

In this equation, X and Y denote the disease infestation—expressed as a % of the untreated control—which is permitted by the two preparations when applied separately. A synergistic effect is present when the fungicidal action of the active compound combination is greater than that of the individual active compounds applied. In this case, the infestation actually observed must be less than the value for the expected infestation (E), calculated from the formula given above.

TABLE E

| *Leptosphaeria nodorum* test / (wheat) protective | | |
|---|---|---|
| Active compound | Active compound concentration the spray liquor in % by weight | Disease infestation as a % of the untreated control |

TABLE E-continued

| *Leptosphaeria nodorum* test / (wheat) protective | | | |
|---|---|---|---|
| (Ia) (known) | 0.01 | 32.5 | |
| (Ib) (known) | 0.01 | 50.0 | |
| (IId) (known) (CAPTAFOL) | 0.01 | 82.5 | |
| (Xb) (known) (FLUBEN-ZIMINE) | 0.025 | 50.0 | |
| (XIV) (known) (ANILAZIN) | 0.005 | 64.8 | |
| | | Observed infestation after application of the mixture as a % of the untreated control | Expected infestation (E) after application of the mixture as a % of the untreated control |
| Mixture of (Ia) and (IId) (mixing ratio 1:1) | 0.01 + 0.01 | 25.0 | 26.8 |
| Mixture of (Ia) and (Xb) (mixing ratio 1:2.5) | 0.01 + 0.025 | 0.0 | 16.3 |
| Mixture of (Ib) and (IId) (mixing ratio 1:1) | 0.01 + 0.01 | 25.0 | 41.3 |
| Mixture of (Ib) and (XIV) (mixing ratio 2:1) | 0.01 + 0.005 | 25.0 | 32.4 |

EXAMPLE F

Drechslera graminea test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

TABLE F

*Drechslera graminea* test (barley) / seed treatment (syn. *Helminthosporium gramineum*)

| Active compound | Amount of active compound applied in mg/kg of seed | Diseased plants as a % of the total number of plants which have emerged |
|---|---|---|
| not treated with the dressing | — | 33.7 |
| (Ib) (known) | 20 | 11.8 |
| (VIIc) (known) BITERTANOL | 100 | 11.6 |
| Mixture of (Ib) and (VIIc) (mixing ratio 1:5) | 20 + 100 | 0.0 |

It is understood that the specification and examples are illustrative but not limitative of the present invention and that other embodiments within the spirit and scope of the invention will suggest themselves to those skilled in the art.

We claim:

1. A fungicidal composition comprising a fungicidally effective amount of a substituted 1-hydroxyethyltriazole of the formula (i)

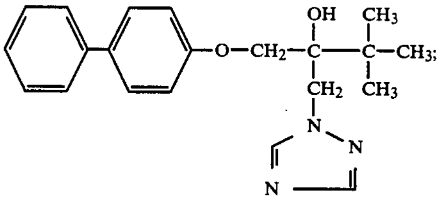

and (ii) a derivative of a triazole of the formula

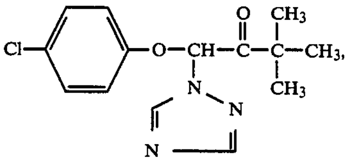

wherein the weight ratio of (i):(ii) is 1:1.

* * * * *